United States Patent [19]

Imran

[11] Patent Number: 5,281,218

[45] Date of Patent: Jan. 25, 1994

[54] CATHETER HAVING NEEDLE ELECTRODE FOR RADIOFREQUENCY ABLATION

[75] Inventor: Mir A. Imran, Palo Alto, Calif.

[73] Assignee: Cardiac Pathways Corporation, Sunnyvale, Calif.

[21] Appl. No.: 894,409

[22] Filed: Jun. 5, 1992

[51] Int. Cl.⁵ ............................................. A61N 1/32
[52] U.S. Cl. ...................................... 606/41; 606/33; 607/154
[58] Field of Search ................... 606/29, 28, 30, 32, 606/33, 41; 128/784, 786, 804

[56] References Cited

U.S. PATENT DOCUMENTS

| | | | |
|---|---|---|---|
| 4,641,649 | 2/1987 | Walinsky et al. | 606/33 |
| 4,800,899 | 1/1989 | Elliott | 128/804 |
| 4,832,048 | 5/1989 | Cohen | 606/41 |
| 4,841,988 | 6/1989 | Fetter et al. | 128/804 |
| 4,913,142 | 4/1990 | Kittrell et al. | 606/16 X |
| 4,998,933 | 3/1991 | Eggers et al. | 606/41 |
| 5,151,096 | 9/1992 | Khoury | 606/17 X |

Primary Examiner—Peter A. Aschenbrenner
Attorney, Agent, or Firm—Flehr, Hohbach, Test, Albritton & Herbert

[57] ABSTRACT

A catheter for use in radiofrequency ablation of the myocardium of the heart of a patient having a flexible elongate member with at least one lumen extending therethrough and having proximal and distal extremities. A needle-like electrode formed of a conducting material is mounted on the distal extremity of the flexible elongate member. A conductor extends through the lumen and is connected to the electrode. Radiofrequency energy is supplied to to said conductor and to the electrode to cause ablation of the myocardium.

9 Claims, 2 Drawing Sheets

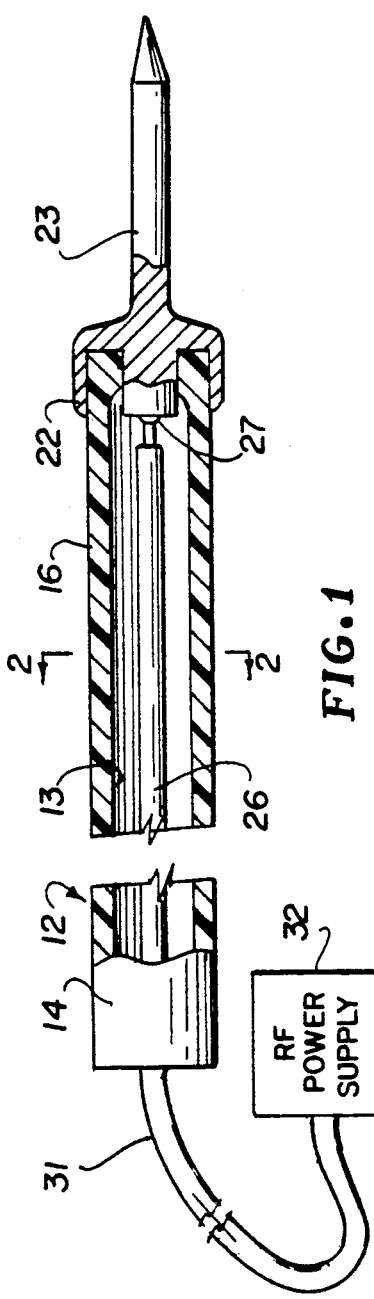
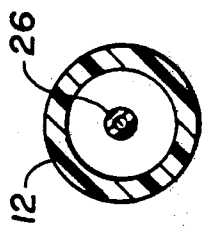
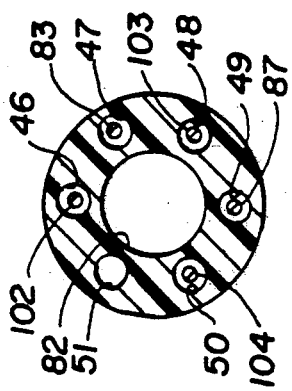
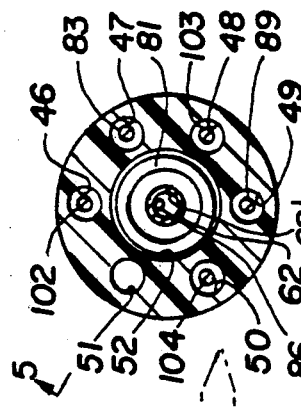
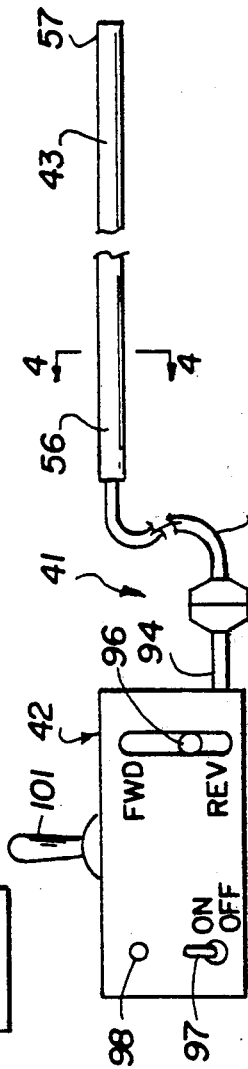
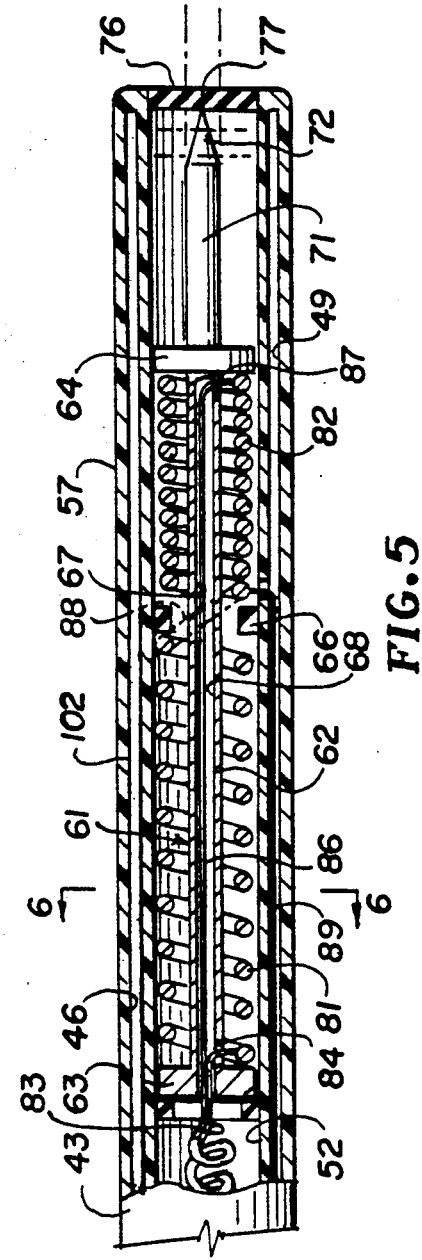

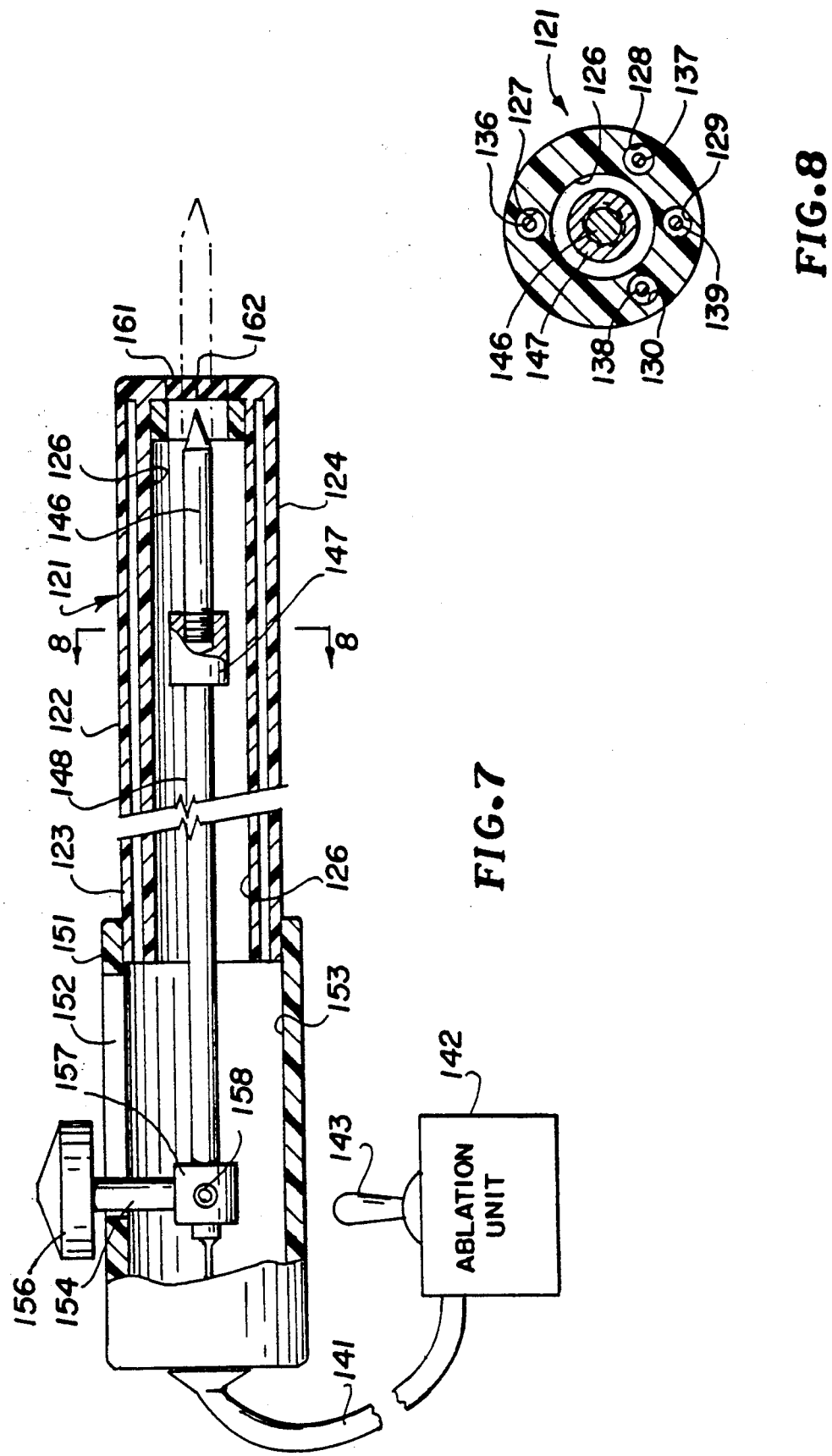

CATHETER HAVING NEEDLE ELECTRODE FOR RADIOFREQUENCY ABLATION

This invention relates to a catheter having a needle electrode for radiofrequency ablation and more particularly to such a catheter for radiofrequency ablation of the myocardium of the heart.

Radiofrequency ablation is being utilized in an attempt to eliminate arrhythmias in the heart by creating lesions in the myocardium of the heart. However it has been found that is has been difficult to create lesions which are large enough and deep enough, particularly in some areas of the heart, as for example in the ventricle where the apex may be as thick as 1 cm and in which aberrant pathway that is causing the arrythmia may be on the epicardial side of the myocardium rather than on the endocardial side. With the present techniques being utilized, the depth of the lesion is limited to 2 to 6 Mm. There is therefore a need for a new and improved catheter making possible deeper and larger lesions in the myocardium of the heart.

In general, it is an object of the present invention to provide a catheter having a needle electrode for radiofrequency of the myocardium of the heart for obtaining deeper and larger lesions in the myocardium.

A further object of the invention is to provide a catheter of the above character in which the same needle is used for penetration and for supplying the RF energy to the myocardium.

Another object of the invention is to provide a catheter of the above character having a needle which is retractable.

Another object of the invention is to provide a catheter of the above character which can be advanced independently of the catheter.

Another object of the invention is to provide a catheter of the above character whose distal extremity can be steered.

Additional objects and features of the invention will appear from the following description in which the preferred embodiments are set forth in detail in conjunction with the accompanying drawings.

FIG. 1 is a side elevational view partially in cross-section showing a catheter having a fixed needle electrode for radiofrequency ablation of the myocardium of the heart.

FIG. 2 is a cross-sectional view taken the line 2—2 of FIG. 1.

FIG. 3 is a side elevational view of the catheter and the controls for use therewith, and a retractable needle electrode in which the distal extremity of the catheter can be steered.

FIG. 4 is a cross-sectional view taken along the line 4—4 of FIG. 3.

FIG. 5 is an enlarged cross-sectional view of the distal extremity of the catheter shown in FIG. 3, and showing the needle electrode in a retracted position.

FIG. 6 is a cross-sectional view taken along the line 6—6 of FIG. 5.

In general, the catheter having a needle electrode for radiofrequency ablation of the myocardium of the heart consists of a an flexible elongate member having at lest one lumen extending therethrough and having proximal and distal extremities. A needle-like electrode formed of a conductive material is secured to the distal extremity of the flexible elongate member. A conductor extends through the lumen and is connected to the electrode. Means is provided for supplying radiofrequency energy to the conductor and to the electrode.

More in particular as shown in FIGS. 1 and 2 of the drawings, the catheter 11 having a needle electrode for radiofrequency ablation of the myocardium of the heart incorporating the present invention consists of a flexible elongate element 12 formed of a suitable material such as plastic which is provided with at least one lumen 13 extending therethrough. The flexible elongate element 12 is provided with proximal and distal extremities 14 and 16. An RF ablation electrode 21 is carried by the distal extremity 16 and is formed of a suitable conductive material such as stainless steel. The electrode is provided with a skirt 22 which extends over the distal extremity 16 of the flexible elongate element 12 and is secured thereto by a suitable means such as an adhesive. The needle electrode 21 provided with a needle 23 which is cylindrical in cross-section that extends distally from the skirt 22. Typically, the needlepoint electrode 23 can have a suitable length such as 1 mm to 10 mm, and a diameter of 0.005 to 0.020 inches.

The flexible elongate element 12 can have a suitable outside diameter such as 0.010 inches. The lumen 13 can have a suitable diameter such as 0.007 inches to provide a wall thickness for the tubular member 12 of approximately 0.0015 inches. A conductor 26 is disposed in the lumen 13 and has a suitable diameter such as 0.004 inches. The conductor 26 can be formed of a suitable material such as copper and has one end connected to the needlepoint 23 by suitable means such as brazing at 27. The conductor 26 exits from the proximal extremity 14 of the flexible elongate element or member 12 and is connected to a cable 31 which is connected to a conventional or radiofrequency power supply 32.

Operation and use of the catheter 11 may now be briefly described as follows. Let is be assumed that a mapping and ablation procedure is underway, as for example in connection with an apparatus and method described in copending application Ser. No. 656,764, filed Feb. 15, 1991, now U.S. Pat. No. 5,156,151, and that mapping has been carried out to ascertain the precise location where it is desired to accomplish ablation. As soon as a desired location has been ascertained, the catheter 11 of the present invention can be advanced through the lumen therein provided in the mapping catheter. Alternatively, it can be advanced outside of the mapping catheter or can be advanced by itself. The catheter 11 can be advanced by pushing on the flexible elongate member 12. As it is being advanced, its progress can be viewed fluoroscopically. Advancement continues until the desired location in myocardium is reached. The catheter is still advanced further to cause the needlepoint 23 to puncture the myocardium to a suitable depth, as for example 2 to 3 mm. As soon as the needle electrode has penetrated sufficiently far, radiofrequency energy is supplied from the power supply 32. Thus, lesions having a depth of 8 mm to 10 mm and having a diameter of approximately 5 mm to 7 mm can be readily achieved to destroy aberrant pathways in the myocardium even though the myocardium may be as thick as 1 cm and the aberrant pathway may be on the epicardial side of the myocardium rather than on the endocardial side.

As soon as the ablation procedure has been completed, the catheter 11 can be removed to complete the procedure.

Another embodiment of the catheter of the present invention which utilizes a retractable needle electrode is shown in FIGS. 3-6. The catheter 41 and the control console 42 for use therewith is shown in FIG. 3. The catheter consists of a flexible elongate member 43 formed of a suitable material such as plastic provided with a plurality of lumens, as for example six lumens 46 through 51 which are spaced circumferentially around the outer margin of the flexible elongate member 43 as shown in FIG. 4, and with a larger central lumen 52. The flexible elongate member 43 is provided with proximal and distal extremities 56 and 57. An actuating member 61 is mounted in the distal extremity 57 for slidable movement within the central lumen 52. The actuator member 61 can be formed of a suitable material such as metal or plastic. It consists of a cylindrical, relatively rigid tube or rod 62 which is provided with a pair of circular disks 63 and 64 at opposite ends which travel longitudinally of the lumen 52 between a circular disk 66 secured to the side wall forming the lumen 52 by a suitable means such as an adhesive. The disk 66 is provided with a hole 67 through which the tube or rod 62 extends. The tube or rod 62 is shown as a tubular member which is provided with an axially extending bore 68.

A needle-like electrode 71 is mounted on the distal extremity of the actuator member 61 and is shown mounted on the disk 64 and extends distally therefrom in alignment with the longitudinal axis of the lumen 52 of the longitudinal axis for the tube or rod 62. As shown, the electrode 71 can be formed integral with the actuator member 61. The needle-like electrode 71 as well as the actuator member 61 can be formed of a suitable electrode-type conducting material. For example, it can be formed of stainless steel or, alternatively, it can be formed of copper which has been gold-plated. The needle-like electrode 71 can have a diameter ranging from 0.005 to 0.020 inches and can have a length ranging from 5 mm. to 1.5 cm. As shown, the needle-like electrode 71 is provided with a sharp point 72. A circular seal 76 is mounted on the distal extremity of the flexible elongate member 43 and is retained therein by suitable means such as an adhesive. The seal 76 is provided with a diametrically extending slit 77 through which the needle-like electrode 71 can extend and retract. The seal 76 serves to prevent liquids such as blood entering the central lumen 52.

Means is provided for advancing and retracting the actuator member 61 with the needle-like electrode 71 carried thereby and consists of helical springs 81 and 82 which are coaxially disposed on the actuator member 61 with the spring 81, its proximal end engaging the disk 63 and having its distal end engaging the disk 66 secured to the flexible elongate member 43. Similarly, the spring 82 has its proximal extremity engaging the disk 66 and has its distal extremity engaging the disk 64. These springs 81 and 82 are formed of a shape memory material such as a nickel-titanium alloy as for example Nitinol.

Means is provided for supplying electrical energy to the springs 81 and 82, and consists of a conductor 86 which is disposed in the lumen 47 and enters into the bore 68 and passes through a hole 84 in the tube 62 and is connected to the proximal extremity of the spring 81. Similarly, a conductor 86 is provided in the lumen 51 and enters into the bore 68 and passes through a hole 87 and is connected to the distal extremity of the spring 82. The proximal extremity of the spring 82 and the distal extremity of the spring 81 are interconnected by a cross link 88 extending through a hole (not shown) in the disc 66. The cross line 88 is connected to a common return conductor 89 disposed in the lumen 49. The conductors 83, 86 and 89 extend to the proximal extremity of the flexible elongate member 41 and are connected into a flexible cable 92 which is provided with a connector 92. The conductors 83 and 86 are provided with coiled portions 83a and 86a to accommodate the reciprocal movement of the actuator member 61. The connector 92 is adapted to be connected to a mating connector 93 connected to another cable 94 which is connected to the control console 42. The control console 42 is of the type described in copending application Ser. No. 07/893,770, filed Dec. 12, 1991, and includes a slide mechanism 96 which can be moved upwardly and downwardly as shown in FIG. 3 to cause movement of the needle electrode 71 between extended and retracted positions by moving it forwardly or rearwardly, or, in other words, in forward and reverse directions. Thus, by supplying energy to the spring 81 by moving the slide mechanism in the reverse direction, the spring 81 is caused to expand to cause compression of the spring 82 and to retract the needle electrode 71 to the position shown in FIG. 5 in which it is disposed behind the seal 76. Conversely, when the slide mechanism 96 is moved toward the forward direction, the spring 82 is caused to expand to extend the needle electrode 72 through the slit 77 provided in the seal 76 and to protrude beyond the distal extremity of the flexible elongate member 43.

The control console 42 is provided with an on-off switch 97, and an indicator light 98 in the form of a light emitting diode to indicate when the power is turned on. The control console is also provided with a joystick 101 which can be pivoted through 360° to cause directional movement of the distal extremity of the flexible elongate member 43. To accomplish this, three elongate elements formed of a material having a negative coefficient of expansion such as Flexinol supplied by Toki of Japan are provided in the lumens 46, 48 and 50 and are connected to conductors 102, 103 and 104 provided respectively in the lumens 46, 48 and 50. These conductors are conducted into the cable 91 and into the connectors 92 and 93 and the cable 94 to be connected to the circuitry provided in the control console 42. As described in copending application Ser. No. 07/793,858, filed on Nov. 18, 1991, the distal extremities of the elongate elements of the material having a negative coefficient are interconnected to the common return conductor 87. As explained in said copending application Ser. No. 07/793,858, filed on Nov. 18, 1991, by operation of the joystick 101 the movement of the distal extremity of the flexible elongate member 43 can be controlled and directed as desired.

The catheter 41 can be utilized for performing an ablation procedure much in the same manner as the catheter 11 shown in FIGS. 1 and 2. It can be utilized with the apparatus for mapping and ablation described in co-pending application Ser. No. 07/656,764, filed Feb. 15, 1991. The catheter has the additional advantage in that the needle electrode 72 while it is being introduced into the vessel of a patient is in a retracted position so that it cannot inadvertently penetrate the side wall of the lumen in which it is being advanced. In addition, the catheter 41 has the advantage in that the distal extremity of the same can be positioned by the use of the joystick 101 so that it can be moved to the desired position as the proximal extremity is advanced by the surgeon. After the mapping operation has determined the area to be ablated, the catheter 41 can be advanced into that position and moved contact with the myocardium. The slide mechanism 96 can then be operated by moving it to the forward position to cause the spring 82 to cause the needle electrode 72 to advance through the slit 77 provided in the seal 76 and to penetrate the myocardium to the desired depth. As soon as the penetration has been accomplished, radiofrequency energy can be supplied from the control console 42 to the needle electrode 72 to perform the desired ablation. As hereinbefore explained, because of the use of the deeply penetrating electrode 72 it is possible to achieve relatively large and deep lesions with relatively small amounts of energy. For example, as hereinbefore described, lesions having a depth of 10 mm. and a diameter of 5-10 mm. can be achieved utilizing as little energy as 15 joules. After the ablation has been performed, the catheter 41 can be removed in a conventional manner.

Another embodiment of a catheter having a needle electrode for radiofrequency ablation is shown in FIGS. 7 and 8. As shown therein, the catheter 121 consists of a flexible elongate member 122 formed of a suitable plastic of the type hereinbefore described which is provided with proximal distal extremities 123 and 124. It is provided with a large central lumen 126 which extends the length thereof and with additional smaller lumens 127, 128, 129 and 130 spaced circumferentially around the central lumen 126. The lumens 127, 128 and 130 are spaced approximately 120° apart. As explained in the previous embodiments to provide steerability of the distal extremity 124, conductors 136, 137 and 138 are provided in lumens 127, 128 and 130 and a return conductor 139 is provided on lumen 129. At least three such conductors are provided which are spaced 120° apart or less. The distal extremities of the conductors 136, 137 and 138 are formed of any material having a negative coefficient of expansion such as Flexinol provided by Toki of Japan. The conductors 136, 137, 138 and 139 are connected by a cable 141 to the power supply 142 which is provided with a joystick control 143 for controlling the movement of the distal extremity 124 of the flexible elongate member 122.

A needle 146 is disposed in the distal extremity of the central lumen 126 is formed of a suitable material such as stainless steel. The needle 146 is provided with a hub 147 which is mounted on the distal extremity of a flexible push-pull wire 148 formed of a suitable material such as stainless steel tubular member as, for example, a hypotube. The tubular member 148 extends the length of the central lumen 126 and extends into a housing 151 mounted on the proximal extremity 123 of the flexible elongate member 122a housing 151 is provided with an elongate slot 152 which opens into a cylindrical recess 153 which receives the proximal extremity of the push-pull wire 148. A slider 154 extends through the recess 154 and is provided with a finger-engaging member 156 on one end disposed and a collar 157 on the other end within the recess 153. The push-pull wire 148 extends through the collar 157 and is secured therethrough by suitable means such as a set screw 158. A seal 161 is provided on the distal extremity of the flexible elongate member 122 and is provided with a slit 162. The seal 161 serves to prevent liquid such as blood from entering the central lumen 126 and permits the needle 146 to be extended and retracted thereto by operation of the slider 154. When the catheter 121 has been advanced into a the desired position and the distal extremity is steered in the manner hereinbefore described by the use of a joystick 143, the needle 146 can be manually advanced into a position to penetrate the myocardium to the desired depth. Radiofrequency energy can then be supplied from the power supply 142 to the needle as described in connection with the previous embodiments. The catheter of the present embodiment is advantageous in that it is relatively simple and the needle can be advanced and retracted manually by the physician. After the ablation procedure has been accomplished, the needle 146 can be retracted by retractor or slider 154. The catheter can then be removed.

In view of the foregoing, it can be seen that there has been provided a catheter which has a needle electrode which can be utilized for radiofrequency ablation of the myocardium of the heart. By utilizing a needle electrode which penetrates deeply into the myocardium it is possible to achieve deep lesions covering a wide area to achieve the desired effect of destroying aberrant pathways to eliminate arrhythmias in the heart. By providing a retractable needle electrode, inadvertent piercing of a vessel wall is eliminated.

What is claimed is:

1. In a catheter for use in radiofrequency ablation of the myocardium of the heart of a patient, a flexible elongate member having at least one lumen extending therethrough and having proximal and distal extremities, a solid needle-like electrode formed solely of a conducting material mounted on the distal extremity of the flexible elongate member, a conductor extending through said lumen and connected to said electrode and means for supplying radiofrequency energy to said conductor and said electrode to cause ablation of the myocardium.

2. A catheter as in claim 1 wherein said needle electrode has a diameter of 0.002 inches to 0.008 inches and has a length ranging from 0.5 to 1 cm.

3. A catheter as in claim 1 wherein said flexible elongate member is sufficiently rigid so that force can be applied to the proximal extremity thereof to cause the needle to penetrate the myocardium.

4. A catheter as in claim 1 together with means carried by the distal extremity of the flexible elongate member for extending and retracting said needle-like electrode.

5. In a catheter for use in radiofrequency ablation of the myocardium of the heart of a patient, a flexible elongate member having at least one lumen extending therethrough and having proximal and distal extremities, a needle-like electrode formed of a conducting material mounted on the distal extremity of the flexible elongate member, a conductor extending through said lumen and connected to said electrode, means for supplying radiofrequency energy to said conductor and said electrode to cause ablation of the myocardium and means carried by the distal extremity of the flexible elongate member for extending and retracting said needle-like electrode; said means for extending and retracting said needle-like electrode including first and second spring members of a material having a negative coefficient of expansion and means for securing said spring members to said needle-like electrode so that when one of the first and second spring members is energized, the needle-like electrode is retracted and when the other of the first and second spring members is energized, the needle-like electrode is extended.

6. A catheter as in claim 4 wherein said means for extending or retracting said needle-like electrode includes push-pull wire having proximal and distal extremities extending through the lumen in the catheter, said needle-like electrode being mounted on the distal extremity of the push-pull wire and means secured to the proximal extremity of the push-pull wire for manually advancing and retracting the same.

7. A catheter as in claim 1 together with a seal disposed on the distal extremity of the flexible elongate element and having a sealable opening therein through which the needle-like electrode can extend and retract.

8. A catheter as in claim 1 together with means for causing as steering movement of the distal extremity of the flexible elongate member.

9. A catheter as in claim 8 wherein said means for causing steering includes at least three elongate elements disposed approximately 120° apart or less within the flexible elongate member and means for selectively applying energy to said flexible elongate elements to cause steering movement of the distal extremity of the catheter.

* * * * *